(12) United States Patent
Yu et al.

(10) Patent No.: US 8,747,317 B2
(45) Date of Patent: *Jun. 10, 2014

(54) FULL-FIELD BREAST ULTRASOUND SYSTEM AND ARCHITECHTURE

(71) Applicant: U-Systems, Inc., Sunnyvale, CA (US)

(72) Inventors: Zengpin Yu, Palo Alto, CA (US); Danhua Zhao, Milpitas, CA (US); Thomas P. Neff, Newark, CA (US); Wei Zhang, Union City, CA (US); Shih-Ping Wang, Los Altos, CA (US)

(73) Assignee: U-Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,064

(22) Filed: Nov. 26, 2012

(65) Prior Publication Data

US 2013/0174412 A1 Jul. 11, 2013

Related U.S. Application Data

(63) Continuation of application No. 10/560,200, filed as application No. PCT/US2004/019488 on Jun. 18, 2004, now Pat. No. 8,317,702.

(60) Provisional application No. 60/480,095, filed on Jun. 20, 2003.

(51) Int. Cl.
*A61B 8/00* (2006.01)

(52) U.S. Cl.
USPC .......... 600/437; 600/440; 600/442; 600/443; 600/446; 600/459; 700/2; 700/3

(58) Field of Classification Search
USPC .................. 600/437–472; 700/2, 3
See application file for complete search history.

(56) References Cited

U.S. PATENT DOCUMENTS

| 5,474,072 | A | 12/1995 | Shmulewitz | |
| 5,479,927 | A | 1/1996 | Shmulewitz | |
| 6,524,246 | B1 * | 2/2003 | Kelly et al. | 600/437 |
| 8,317,702 | B2 * | 11/2012 | Yu et al. | 600/437 |

FOREIGN PATENT DOCUMENTS

| DE | 19753571 A1 | 6/1999 |
| DE | 19902521 A1 | 7/2000 |

OTHER PUBLICATIONS

Foster F. S. et al. "The Ultrasound Macroscope: Initial Studies of Breast Tissue" Ultrasonic Imaging USA, vol. 6, No. 3, Jul. 1984, pp. 243-261.

European Search Report dated Jan. 29, 2007 in connection with European Patent Application No. 03 73 4336.

* cited by examiner

Primary Examiner — James Kish
(74) Attorney, Agent, or Firm — Alleman Hall McCoy Russell & Tuttle LLP

(57) ABSTRACT

A modular, flexible architecture for offering full-field breast ultrasound (FFBU) functionality and general-purpose ultrasound functionality in a single system is described. A conventional, general-purpose ultrasound system is modified with an FFBU toolkit to create a dual-capability ultrasound system, the dual-capability ultrasound system being able to accommodate both general-purpose ultrasound functionality and FFBU functionality, using a single ultrasound engine. Among other advantages, real-world clinical environments may enjoy cost savings for initial system procurement, space savings on clinic floors, easier and less expensive system upgrades, and the ability to use a single system and user interface for both FFBU screening and for follow-up diagnosis, biopsy, etc. Among other advantages from an ultrasound manufacturer's perspective are the ability to quickly and/or more easily come to market with an FFBU-related offering by modifying their existing general-purpose ultrasound systems with FFBU toolkits to quickly create dual-capability ultrasound systems.

20 Claims, 10 Drawing Sheets

Type Definitions enum EImagingModes { kModeB, kModeBColorFlow, kBModeColorPower, ... };
enum EImagingControls { kDGC1, ..., kDGCn, kGainB, kDepth, kFOV, kFOVMode, ... };
enum EConvertModes { kNearestNeighbor, kBilinearInterpolation, ... };
struct SProbeParameters { std::string sProbeName, int iNumElements, double dElementPitchMM, ...};
struct SAlarmStatus { BOOL PowerStatus, int iCageTemperature, ... };

Imaging Control

Initialize();
    *Initializes the imaging system, including loading the probe tables and establishing communication to the embedded system.*
Terminate();
    *Shuts down communication to the embedded system and powers it off.*
vector< std::string> ReadProbeConnectorStatus();
    *Retrieves a vector of length equal to the number of probe connectors. Each entry contains the name of the probe installed in that connector or " " if no probe is installed.*
SelectProbeConnector( int iConnector );
    *Enables the probe in the specified connector to acquire images and enables the probe table for that probe.*
SProbeParameters GetProbeParameters( std::string sProbeName );
    *Returns the probe parameters for the probe with the specified ProbeId.*
int GetActiveProbeConnector( );
    *Returns the connector index of the currently enabled probe.*
vector< std::string> GetApplicationList( std::string sProbeName );
    *Returns the list of the applications supported for the specified probe ID.*

*FIG. 8A*

Imaging Control (cont.)

vector< std::string> GetSubApplicationList( std::string sProbeName,
        std::string sApplicationName );
    *Returns the list of the sub applications supported for the
    specified probe ID and application.*
SelectProbeApplication( std::string sApplicationName, std::string
        sSubApplicationName );
    *Selects the probe program associated with the specified
    program name for the currently selected probe.*
SetImagingMode( EImagingModes );
    *Set the imaging mode to the specified mode.*
EImagingModes GetImagingMode( );
    *Returns the currently active imaging mode.*
SetImagingControl( EImagingControls eImagingControl, double dValue );
    *Sets the specified user imaging control to the specified value.*
ApplyImagingControls( );
    *Applies the current set of imaging controls to the imaging HW.
    Blocks until the parameters are completely applied to the
    imaging HW.*
double GetImagingControl( EImagingControls eImagingControl );
    *Returns the current setting of the specified imaging control.*
const SDisplayParameters GetDisplayParameters( );
    *Read the current set of derived display parameters.*
Freeze( BOOL bFreeze );
    *Immediately freezes or unfreezes imaging, retaining the current
    imaging mode. Unfreeze will automatically apply any controls
    that are still pending.*
BOOL GetFreezeStatus( );
    *Returns the current freeze state.*
SAlarmStatus GetAlarmStatus( );
    *Returns the current front end alarm status.*
Attach( Aspect aNotificationAspect );
    *Attaches for notification on the specified aspect. Aspects
    include:
    Probe Inserted Or Removed
    Front End Alarm*

---

Diagnostics / Engineering Tools

LoadProbeFile( );
    *Reloads and applies the probe table for the active probe using the
    currently selected probe program.*

*FIG. 8B*

FULL-FIELD BREAST ULTRASOUND SYSTEM AND ARCHITECHTURE

CROSS-REFERENCE TO RELATED APPLICATIONS

This application is a continuation of U.S. Application Ser. No. 10/560,200, filed Sep. 9, 2010, now U.S. Pat. No. 8,317, 702 issued on Nov. 27, 2012, which is a national stage of PCT International Application No. PCT/US2004/19488, filed Jun. 18, 2004, now published as WO/2004/112577 Jun. 18, 2004, which claims the benefit of U.S. Provisional Application No. 60/480,095, filed Jun. 20, 2003, the entire contents of each of which are incorporated herein by reference.

The subject matter of this disclosure is also related to the subject matter of the following patent application: U.S. Ser. No. 60/439,437 filed Jan. 9, 2003; U.S. Ser. No. 60/429,728 filed Nov. 27, 2002; U.S. Ser. No. 10/305,661 filed Nov. 27, 2002, now U.S. Pat. No. 7,103,205 issued Sep. 5, 2006; U.S. Ser. No. 10/305,936 filed Nov. 27, 2002, now U.S. Pat. No. 7,597,663 issued Oct. 6, 2009; U.S. Ser. No. 60/415,385 filed Oct. 1, 2002; U.S. Ser. No. 10/160,836 filed May 31, 2002, now U.S. Pat. No. 7,556,602 issued Jul. 7, 2009; International Application Ser. No. PCT/US01/43237 filed Nov. 19, 2001, now published as WO2002/0043801; U.S. Ser. No. 60/326, 715 filed Oct. 3, 2001; and U.S. Ser. No. 60/252,946 filed Nov. 24, 2000, each of which is incorporated by reference herein. These applications are collectively referred to herein as the "Incorporated FFBU Applications."

FIELD

This patent specification relates to medical imaging systems and processes. In particular, the present invention relates to methods, systems, methods of doing business, and architectures for full-field breast ultrasound technology.

BACKGROUND

Full-field breast ultrasound (FFBU) generally refers herein to the acquisition, processing, and/or display of breast ultrasound information as described in one or more of the Incorporated FFBU Applications identified supra. Most generally, the FFBU process includes acquiring volumetric ultrasound scans of a breast in a standard and repeatable manner, processing the volumetric data to form thick-slice images therefrom, and displaying the thick-slice images to a clinician. More preferably, the FFBU process is used as an adjunct to conventional x-ray mammography, with the thick-slice images corresponding to slab-like regions of the breast substantially parallel to standard x-ray mammogram view planes (e.g., CC, MLO) and being displayed simultaneously with one or more x-ray mammograms taken along those standard x-ray mammogram view planes. The FFBU process is also highly amenable to computer-aided detection (CAD) analysis, with CAD algorithms being performed on the three-dimensional volumetric ultrasound data, the two-dimensional thick-slice images, the x-ray mammogram data, or any combination thereof. Although directed primarily to forming the three-dimensional ultrasound volumes from B-mode scans, the FFBU process can be amenable to a variety of different ultrasound-based tissue imaging strategies including, for example, color Doppler, power Doppler, and vibrational resonance techniques.

In one or more of the Incorporated FFBU Applications, configurations are described in which ultrasound engines are integral with the FFBU acquisition systems and their associated system control/user interface systems. The ultrasound engines associated with those configurations are dedicated to FFBU operation only, and are not part of regular, general purpose ultrasound systems.

A problem can arise in that if a particular clinic wished to have both FFBU functionality and general purpose ultrasound functionality, they would need to procure, operate, and maintain two separate systems having two separate ultrasound engines. In practical use, the clinician would need to go back and forth between using the two separate systems, for example, using the FFBU for initial patient screening and then using the separate general-purpose ultrasound system for follow-up diagnosis, biopsy, or the like. From a manufacturing perspective, there would need to be two different product design cycles, implementation cycles, etc., for the two distinct systems. Moreover, if significant improvements were made, for example, in the capabilities of the ultrasound engine of the general purpose ultrasound system, the manufacturer(s) would need to make—and the clinics would need to buy—two separate upgraded systems to enjoy these advancements in both the general-purpose and FFBU systems.

Accordingly, it would be desirable to provide a method and systems that at least partially obviates one or more of the impractical and/or inefficient scenarios described above.

SUMMARY

According to a preferred embodiment, a modular, flexible architecture is provided for offering full-field breast ultrasound (FFBU) functionality and general-purpose ultrasound functionality in a single system, with improved practical implications for both real-world clinical environments and real-world ultrasound system manufacturing environments. A system, method, method of doing business, and architecture are provided in which a conventional, general-purpose ultrasound system is modified with an FFBU toolkit to create a dual-capability ultrasound system, the dual-capability ultrasound system being able to accommodate both general-purpose ultrasound functionality and FFBU functionality, using a single ultrasound engine. Among other advantages, real-world clinical environments may enjoy cost savings for initial system procurement, space savings on clinic floors, easier and less expensive system upgrades, and the ability to use a single system and user interface for both FFBU screening and for follow-up diagnosis, biopsy, etc. Among other advantages from an ultrasound manufacturer's perspective are the ability to quickly and/or more easily come to market with an FFBU-related offering, by modifying their existing general-purpose ultrasound systems with FFBU toolkits to quickly create dual-capability ultrasound systems.

The present specification further relates to particular enhancements to an FFBU system, whether it be a dual-capability ultrasound system described above or a monolithic, integrated FFBU system, for improving volumetric ultrasound data acquisition (and the quality of the resulting thick-slice images) near the skinline of the breast. In one preferred embodiment, a pre-formed gel block is provided that is specially shaped to fill in air gaps between the breast periphery and the upper and lower compressive members of an FFBU scanning device. The present specification further relates to FFBU system enhancements in the area of color Doppler imaging, wherein color Doppler frames are acquired in real time for suspicious lesions (or otherwise interesting regions of the breast) identified from the initial B-mode volumetric scans of the breast taken by the FFBU.

BRIEF DESCRIPTION OF THE DRAWINGS

FIGS. 8A and 8B illustrate components of an imaging system application program interface (API) for an off-the-shelf ultrasound engine according to a preferred embodiment.

DETAILED DESCRIPTION

Figure 1:
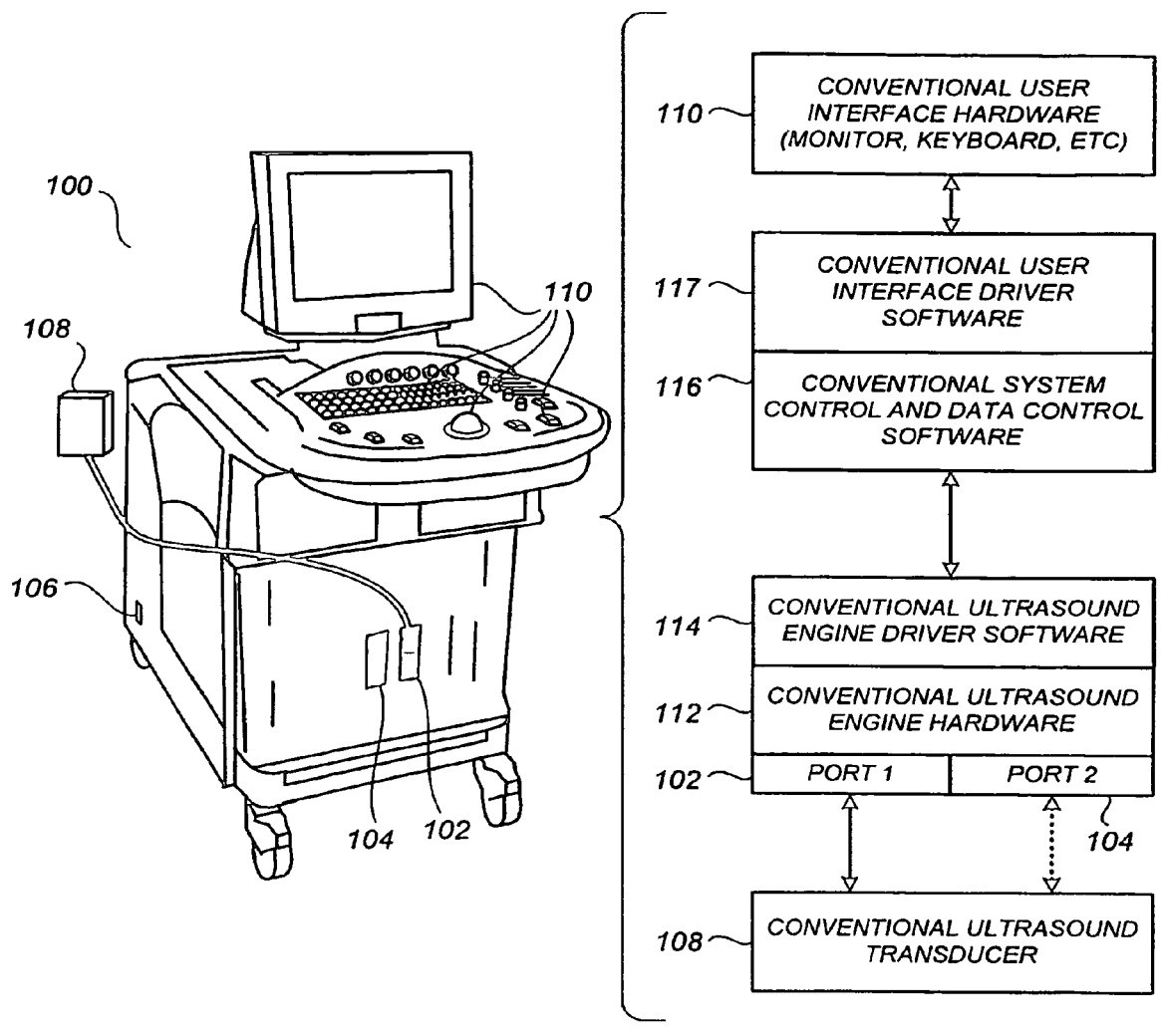
FIG. 1 illustrates an exterior and conceptual architectural view of a general purpose ultrasound system.

FIG. 1 illustrates an exterior and conceptual architectural view of a general purpose ultrasound system (GPUS) 100 according to the prior art. As laid out in FIG. 1, the general purpose ultrasound system 100 is similar to many different commercially available systems such as those provided by Siemens, General Electric, Toshiba, or a variety of other manufacturers. As known in the art, typical examples of general-purpose ultrasound systems include the Siemens Sono-Line Antares and the Siemens Acuson Sequoia, and can be characterized as facilitating ultrasonic imaging using a hand-held probe in conventional environments such as cardiac, neonatal, thoracic, and the like. As used herein, the term off-the-shelf ultrasound engine refers to the ultrasound engines used in such general purpose ultrasound systems.

The GPUS 100 comprises a first transducer port 102, a second transducer port 104, and a miscellaneous communications interface 106 (such as a USB, Firewire, RS-232, etc.). The miscellaneous communications interface 106 is commonly a by-product of most conventional system architectures that are based on a standard PC architecture (e.g., systems with Intel Pentium-class processors and Windows operating systems). The miscellaneous communications interface 106 often goes unused, although it is usually readily accessible via standard Windows operating system interfaces. In some cases, even if the miscellaneous communications interface 106 is not directly accessible on an exterior port of the GPUS 100, it can be accessed indirectly by removing a side or rear panel of the GPUS 100 which exposes therein PC-based hardware having such a communications port. GPUS 100 further comprises a conventional transducer 108 connected to the first transducer port 102, and user interface hardware 100 (display, keyboard, trackball/mouse, various extra key/knob inputs, etc.)

From a conceptual architecture viewpoint, the GPUS 100 comprises an ultrasound engine formed from (i) a hardware platform 112 that is PC-based, usually with auxiliary boards plugged into a PCI or other system bus that perform specialty ultrasound hardware duties known in the art, such as beamforming, and (ii) proprietary ultrasound engine driver software 114 that drives the specialty hardware via the PC-based operating system. The OPUS 100 further comprises "higher-level" system control and data control software 116, also running on the PC-based system, that accepts vector ultrasound data from the ultrasound engine, manipulates the vector data into viewable ultrasound image data, and otherwise manages the system. The GPUS 100 further comprises user interface software 117, also running on the PC-based system, that performs the ultimate formatting and outputting of the ultrasound image data, and that receives user commands for controlling the overall GPUS 100.

Although provided to customers only in the form of monolithic blocks of executable code sitting inside the GPUS 100, the ultrasound engine driver software 114, the system and data control software 116, and the user interface software 117 is almost always designed and programmed separately in a modular fashion using object-oriented programming techniques in languages such as C++. As known in art, for virtually all ultrasound system manufacturers, the source code is naturally segregated in fashions identical or similar to that shown in FIG. 1. Indeed, it is commonly the case that the ultrasound engine driver software 114 is developed by an entirely different group of programmers than the system and data control software 116/user interface software 117. The ultrasound engine driver software 114 is "exposed" to the data control software 116 by virtue of APIs (application programming interfaces) that define the methods and data objects that can be invoked to achieve the desired functionalities. In this manner, provided that the APIs to the ultrasound engine remain well defined and properly called by the higher-level routines, the different software modules 114, 116, and 117 can be developed, improved, and perfected separately and with greater efficiency than if treated as one big, monolithic program.

Figure 2:
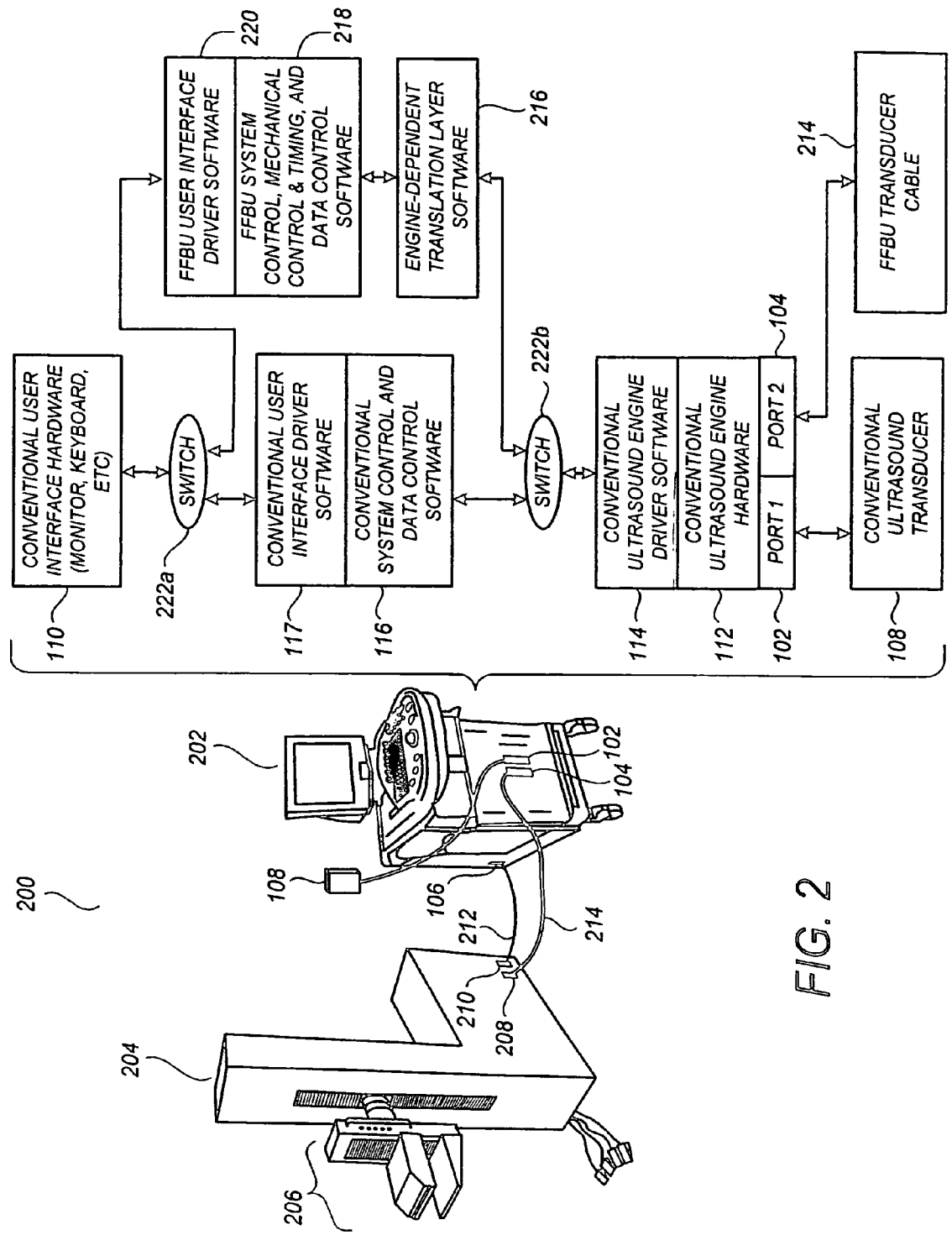
FIG. 2 illustrates an exterior and conceptual architectural view of a dual-capability ultrasound system designed and manufactured using an FFBU toolkit according to a preferred embodiment.

FIG. 2 illustrates an exterior and conceptual architectural view of a dual-capability ultrasound system 200 that, according to a preferred embodiment, is designed and manufactured using an FFBU toolkit that harnesses the modularity of the GPUS 100. The dual-capability ultrasound system 200 comprises a modified general purpose ultrasound unit (MGPUS) 202 similar to the GPUS of FIG. 1 except that (i) its software has been augmented with additional modules 216-222b as described herein, (ii) one of its transducer ports has been connected to an FFBU probe system described infra, and (iii) it has been connected to an FFBU scanning apparatus 204 via the miscellaneous communications port 106.

Generally speaking, the FFBU scanning apparatus 204 is similar to at least one of those described in the Incorporated FFBU Applications, supra. However, in a preferred embodiment, the FFBU scanning apparatus 204 contains primarily only the mechanical scanning features of an FFBU system (stepper motors, fluid pumps, compression plates, transducer movement mechanisms, etc.) and control processor(s) that control these mechanical systems according to commands received over a communications cable 212 via a communications port 210. FFBU scanning apparatus 204 comprises a special FFBU transducer that plugs into the second transducer 104 of the MGPUS 202 via a connector 208 and a conventional transducer cable 214. Notably, the conventional ultrasound scanning engine portion 112/114 of the MGPUS is unchanged from that of the GPUS, and "thinks" that it is driving a conventional ultrasound probe even when it is driving the special FFBU transducer. The special FFBU transducer is contained within the upper (and/or lower) breast compression housing of the compression/scanning apparatus 206, as described in the Incorporated FFBU Applications, supra.

It is to be appreciated that the FFBU toolkit, in other preferred embodiments, is not required to have a mechanical scanning apparatus identical in structure and/or scanning strategy similar to the particular mechanical scanning apparatus 204 of FIG. 2. In other preferred embodiments, the mechanical scanning process can be done using the other methods described in the Incorporated References that can mechanically obtain repeatable scans of the breast volume, such as the supine-patient adapter and the face-down reservoir-type adapters described in several of the Incorporated References.

The dual-capability ultrasound system 200 is formed by providing an ultrasound system manufacturer of the GPUS 100, or a third-party in privity therewith, with an FFBU toolkit that allows quick and easy design and manufacture of the dual-capability ultrasound system 200. Of course, other business arrangements based on different sources/combinations of the GPUS 100/FFBU toolkit could readily be achieved in view of the present disclosure and are within the scope of the preferred embodiments. In one preferred embodiment, the FFBU toolkit comprises the FFBU scanning apparatus 204, the data/transducer cables 212/214, a computer program product that is preferably in source code format such as C++, and an FFBU toolkit interface software specification that defines APIs required to be invoked from the computer program product. An example of such software APIs is illustrated in FIG. 8.

The computer program product of the FFBU comprises a first module 218 for FFBU system control, mechanical control and timing of both the FFBU scanning apparatus 204 and the ultrasound engine 112/114, and data control consistent with the functionalities described in the Incorporated FFBU Applications, supra. The computer program product of the FFBU further comprises a second module 220 for driving a user interface for the FFBU functionality. The FFBU user interface can include outputs consistent with any of those described in the Incorporated FFBU Applications, supra. In one preferred embodiment, these FFBU outputs are displayed on a monitor provided in the GPUS user interface hardware 110, while in another embodiment they are provided on a separate or additional display (not shown). Optionally, a real-time CAD algorithm module can also be provided for performing real-time CAD algorithms on the acquired data.

To properly integrate the FFBU toolkit with the GPUS 100, it will be necessary for the builder of the dual-capability ultrasound system 200 to construct an engine-dependent translation layer software 216 based on the information provided in the FFBU toolkit interface software specification (see e.g., FIG. 8), together with a knowledge of the conventional ultrasound engine APIs of the GPUS 100. In an alterative preferred embodiment, the provider of the FFBU toolkit is provided with the knowledge of the conventional ultrasound engine APIs of the GPUS 100, and then creates the engine-dependent translation layer software 216 for providing with the FFBU toolkit. In still another preferred embodiment, there is a joint development agreement between the builder of the dual-capability ultrasound system 200 and the provider of the FFBU toolkit to co-develop the engine-dependent translation layer software 216.

According to a preferred embodiment, the dual-capability ultrasound system 200 can be switched in real time by the user/clinician between (i) a regular mode of operation provided by the GPUS 100 capabilities using modules 116-117, to (ii) an FFBU mode that invokes modules 216-220 instead. This is performed by switches 222a and 222b, which operate in unison. The switches 222a and 222b can be controlled by a software switch invoked by a simple selection of an omnipresent and always-on-top soft-button on the user display, or can be controlled by a hardware switches located on the user display. From a software coding perspective, it is expected that these switches are very easily implemented in one or two lines of code near the main entry point of the top-level GPUS software module.

The special FFBU transducer referred to supra comprises a very long array, e.g. 15 cm long, of transducer elements. The FFBU transducer generally is much longer and has more elements than commonly used with GPUS 100. According to a preferred embodiment, field-programmable gate array (FPGA) logic is included in the FFBU transducer that provides a "sliding window" effect such that only a predetermined number of elements are active at any time, along a subset of the length. After obtaining one or more lines of scan data associated with the present window position, the window is moved by the FPGA logic responsive to commands from the ultrasound engine hardware and the process is repeated until the end of the array is reached. Notably, the presence of a "sliding window" along the transducer length is transparent to the ultrasound engine, and is handled by the timing circuitry of the FPGA in combination with the software module 218.

According to another preferred embodiment, a pre-formed gel block is provided that is specially shaped to fill in air gaps between the breast periphery and the upper and lower compressive members of an FFBU scanning device. This has been found to substantially improve volumetric ultrasound data acquisition near the skinline of the breast. In one preferred embodiment, the gel material is similar to that described in U.S. Pat. Nos. 4,369,284, 4,618,213, and 5,262,468 and referenced in U.S. Pat. No. 5,664,573, except that the gel is modified so as to be sufficiently stiff or non-fluid in nature (having the consistency of Jell-O, for example, but being much more durable) so that it can retain shapes illustrated, for example, in FIG. 3. The U.S. Pat. Nos. 4,369,284, 4,618,213, 5,262,468 and 5,664,573 are incorporated by reference herein. An FFBU clinic can be provided with an array of pre-formed gel blocks for different breast sizes, thicknesses, and compressibilities.

The present specification further relates to FFBU system enhancements in the area of color Doppler imaging, wherein color Doppler frames are acquired in real time for suspicious lesions (or otherwise interesting regions of the breast) identified from the initial B-mode volumetric scans of the breast taken by the FFBU. In one preferred embodiment, an operator of the FFBU system examines thick-slice images and/or volumetric data output in real time, and then commands the FFBU scanning apparatus to return to a particular region and perform color Doppler scans thereon. The color Doppler frames are decimated with respect to both (i) two-dimensional resolution within acquired slices, and/or (ii) distance between acquired slices, as compared to the B-mode scans, such that any patient discomfort associated with an extended breast compression session is mitigated. A minimum acceptable color Doppler resolution should be maintained, however. In another preferred embodiment, CAD algorithms on the thick-slice images and/or volumetric data is automatically performed and, upon location of a suspicious lesion or other interesting region, the FFBU scanning unit is automatically sent back to those locations to perform Doppler scans, without requiring any operator input.

These and other aspects of the preferred embodiments are further described below.

Field. Medical ultrasonic imaging instrument for full field breast image acquisition.

Object. A flexible and detachable full field breast mechanical scanner hardware and system control software protocol Features. Known full breast scanners, such as a water-bag breast scanner made by Labsonics and an immersion breast scanner made by Ausonics, all used a dedicated ultrasound data acquisition system and dedicated ultrasound transducers. These systems integrated mechanical scanner and ultrasound system together to generate static longitudinal or cross section images, it is very difficult to perform dynamic diagnostic examinations. This disclosure regards keeping the ultrasound system and mechanical scanner as separated units.

Ultrasound System. One or multiple full field breast transducers ($\geq 70$ mm) are connected to the ultrasound system. The ultrasound image acquisition system controls the movement of transducer, and synchronizes the ultrasound image acquisition. A static 3D full breast image data is acquired. A hand-held transducer is connected to one of ultrasound system transducer ports. Because the ultrasound system user interface is not changed, this hand held transducer can perform real time ultrasound breast exam Full field breast mechanical scanner. The full field breast ultrasound transducers are mounted on the scanner. Scanner receives commands from the ultrasound system, which synchronizes the transducer movement and image acquisition. Scanner sends status and scanner control parameters back to the ultrasound system. The status provides system diagnostic information. The control parameters can be used for breast image analysis. The full field breast ultrasound systems can be, but are not limited to the following, compression plate (Mammography like) breast scanner; water bag breast scanner, immersion breast scanner.

Full Field Breast Transducer. The transducer assembly consists of two major parts. Acoustic module, which converts electrical signals to acoustic waves and vise versa. The module can be linear array, linear and curved array, phased array, varying pitching array, 1.5 D array, or 2 D array. And a programmable multiplexer which can interface with different ultrasound systems to perform image acquisition.

Ultrasound beamformer independent software. In order to control full breast scanner from an ultrasound system as well as providing the capability of performing diagnostic hand-held breast scans, an ultrasound beamformer independent software package is developed. This software defines a generic interface from the application control software to the ultrasound beamformer. The application control software can interface to different beamformers by linking to the beamformer specific library developed to conform to the generic interface.

Seamless transition between automated full-field breast and hand-held diagnostic ultrasound scanning. The application software allows for seamless transition between these two modes of operation. The user interface provides the operator the ability to select between several transducers attached to different ports of the beamformer. Selecting a full-field breast transducer associated with a motor in the full-field breast mechanical scanner (the default selection after system initialization) activates the automated full-field breast scan mode of operation. Selecting any other transducer activates the hand-held diagnostic scan mode of operation. The latter mode of operation can also be activated on any transducer in service mode.

The advantages of the disclosed embodiments include the following. The ultrasound system and mechanical scanner are separated units, which allows the mechanical scanner to be attached to different ultrasound systems. A hand held transducer can be used for diagnostic ultrasound exams without any conventional ultrasound system modifications. Acoustic module of full field breast transducers are independent of ultrasound systems. The interface to different ultrasound systems is provided by the programmable multiplexer inside the transducer. Linear and curved array, and varying pitch array transducers increase field of view without increasing number of elements.

Color Doppler can be performed on the full breast. This can be done in following ways. After performing full breast scan, compound thick slice images are generated. User can point to the lesion on the thick slice images, then, transducer can automatically move to the lesion area. Color Doppler ultrasound is performed to show lesion vascularity. More importantly, Color Doppler is performed on the exact lesion detected by full breast scan. After a full breast scan is done and a lesion is detected, a radiologist can use hand held transducer to scan lesion area while breast is in compression. This method gives more flexibility because a radiologist can move hand held transducer at different direction.

Figure 4:
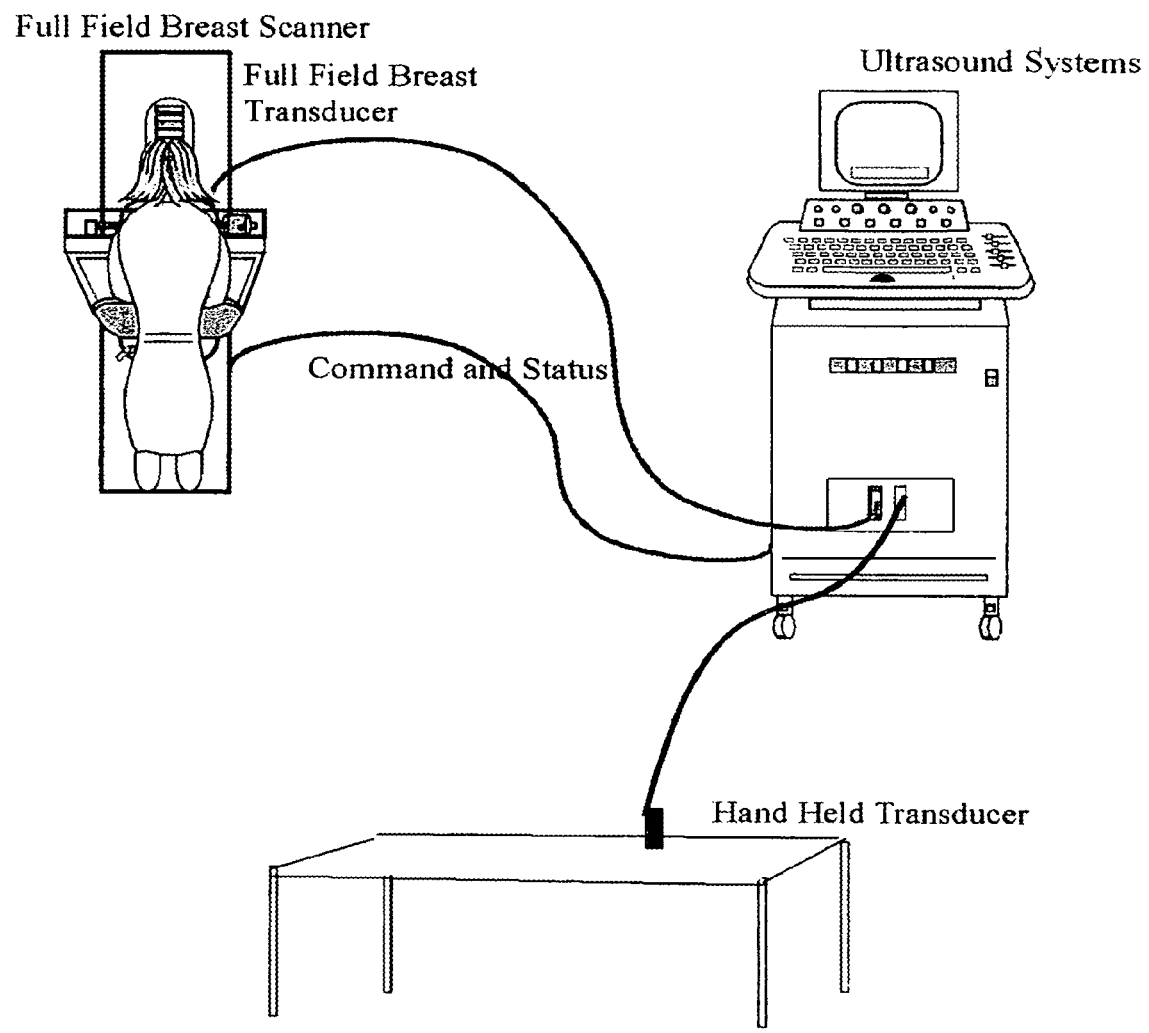
FIG. 4 illustrates a perspective view of a patient receiving an FFBU scan using the dual-capability ultrasound system of FIG. 2.
Figure 5:
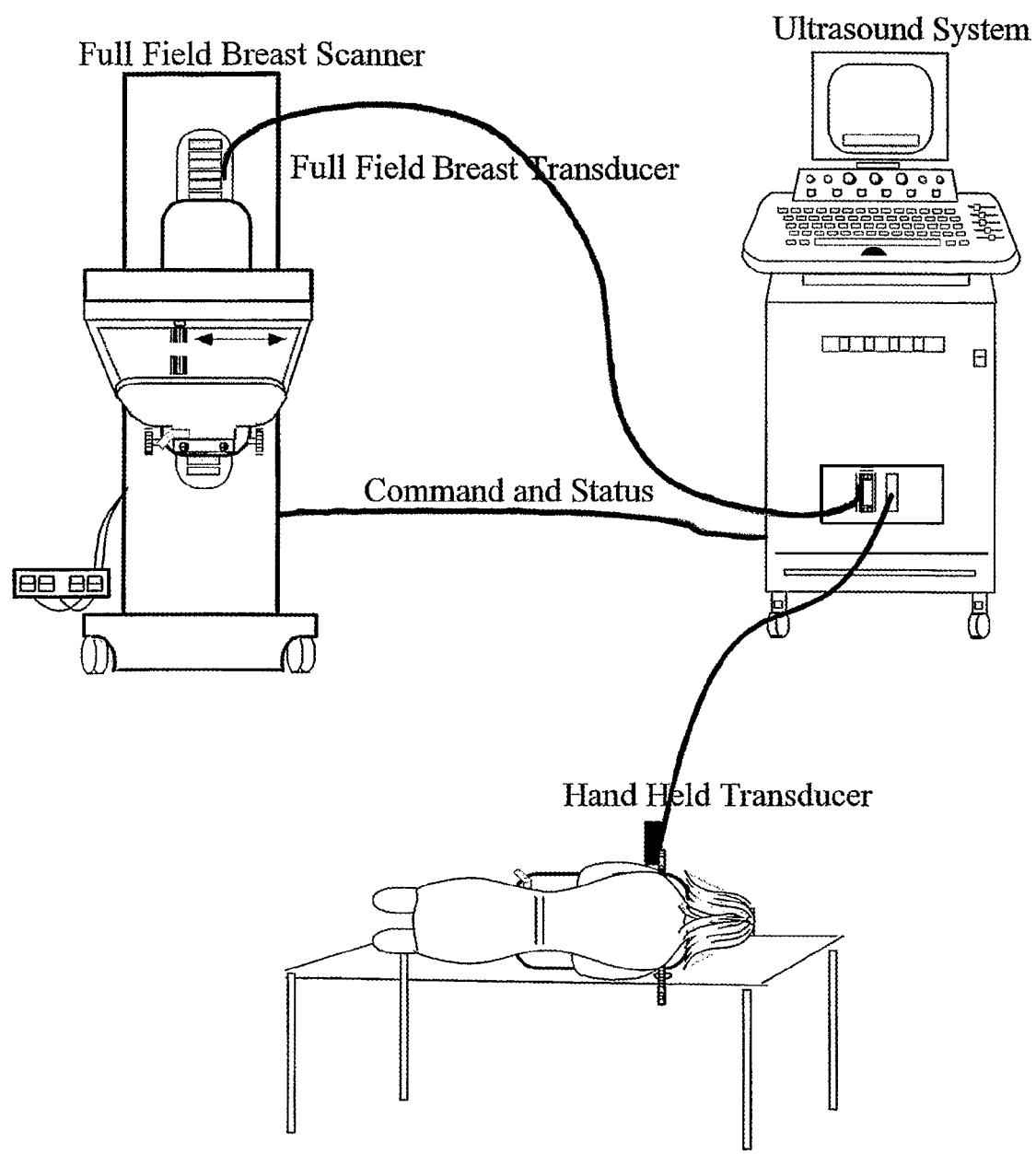
FIG. 5 illustrates a perspective view of a patient receiving a hand-held breast ultrasound scan using the dual-capability ultrasound system of FIG. 2.

Breast diagnostic ultrasound can be performed after full breast scan. After a full breast scan is done (FIG. 4), and a lesion is detected. Patient can lay down on a bed, a radiologist can use hand held transducer to perform a breast diagnostic ultrasound procedure (FIG. 5). Full breast scan provides an accurate orientation where lesion is located.

Figure 3:
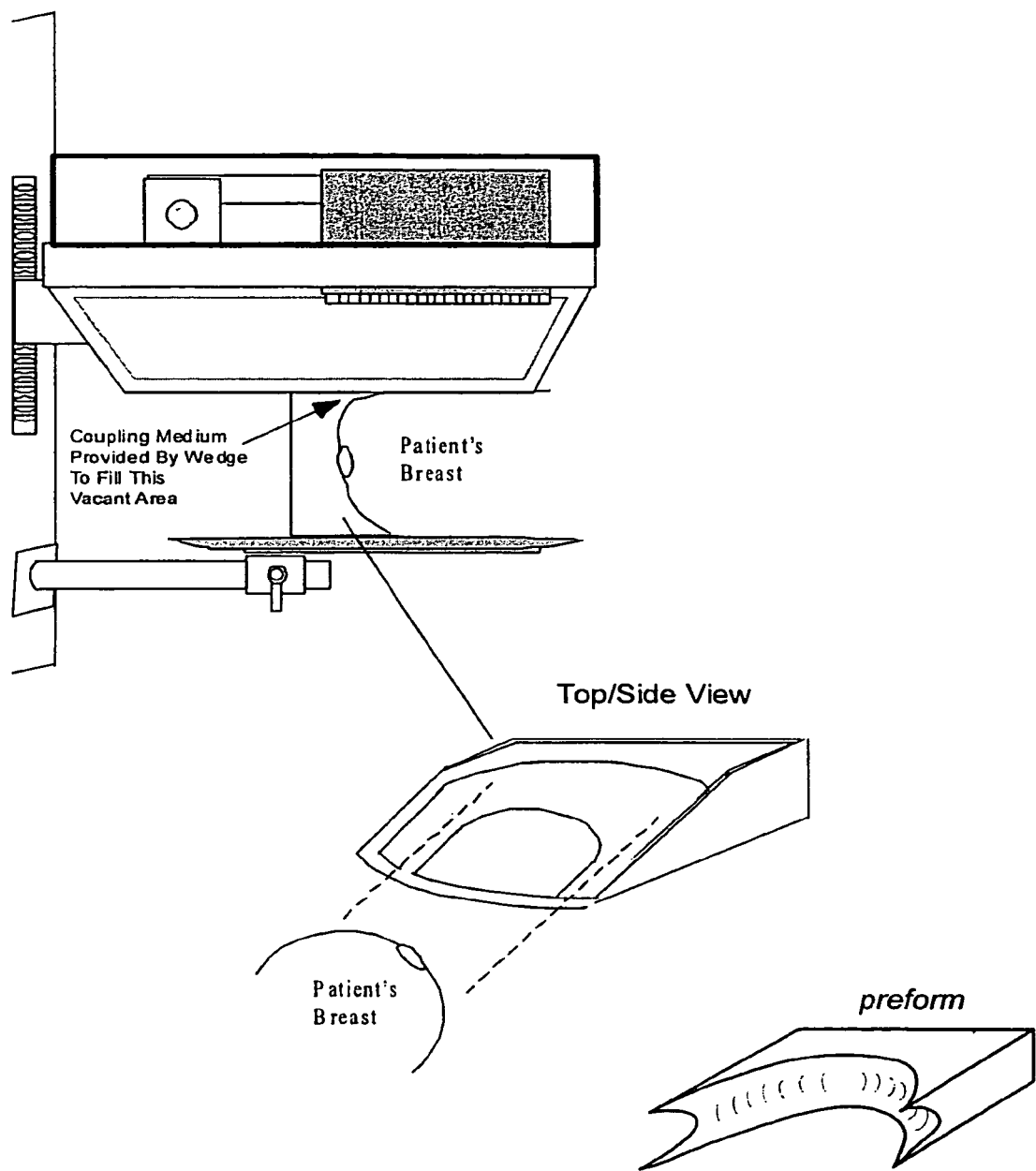
FIG. 3 illustrates a preformed gel pad and its use in an FFBU scanning apparatus according to a preferred embodiment.

In this section, only compression plate full breast scanner is discussed. Full-Field Breast scanning device and a conventional ultrasound system are separated units. Ultrasound system controls whole breast scan. The operator activates the machine so that a pair of plates applies pressure to the breast similar to a mammography machine. A soft and elastic gel pad is made in a horseshoe shape (FIG. 3). It is placed between breast and compression plate. Gel pad can fill in between breast roll off area and compression plate. It makes contact between breast tissue and compression plate, so that the breast roll off area can be imaged. For flatbreast tissue area, gel pad is cut off, breast can make direct contact with compression plate. Due to the acoustic property of gel pad, adding gel pad may reduce image penetration and change breast tissue speckle pattern or image resolution. The horseshoe sharp of gel pad allows flat breast tissue area making a direct contact with compression plate, which does not introduce image artifacts.

Once the breast has been immobilized between the plates, the operator initiates the scan from ultrasound system. A computer-controlled motor moves, an ultrasound probe across one of the two plates. A 2D B-Mode image is acquired by ultrasound system when the transducer transmits and receives ultrasound signals that pass through the plate and travel inside the breast. As the machine moves the probe, a three-dimensional image volume is collected.

In order to make a flexible and detachable Full-Field Breast scanner, which can interface with any conventional ultrasound system, a set of hardware, software and transducer interface protocol are created.

Electronic Interface. Standard hardware communication protocol is used to link Full-Field Breast mechanical scanning device and conventional ultrasound system. The communication link can be serial links (RS-232 or USB, Firewire or local area network interface).

Transducer Interface. Because the ultrasound beam transmit and receive control schemes are different between conventional ultrasound systems, in order to make connection from full breast ultrasound transducer to those ultrasound systems, a programmable electronics device is embedded in transducer. This programmable device can use, but not limited to, the following control signals for communication: Acoustic beam position; Acoustic beam aperture size; Start of Frame; Start of transmit; Start of receive; Programming clocks; Feedback data to ultrasound system.

Figure 6:
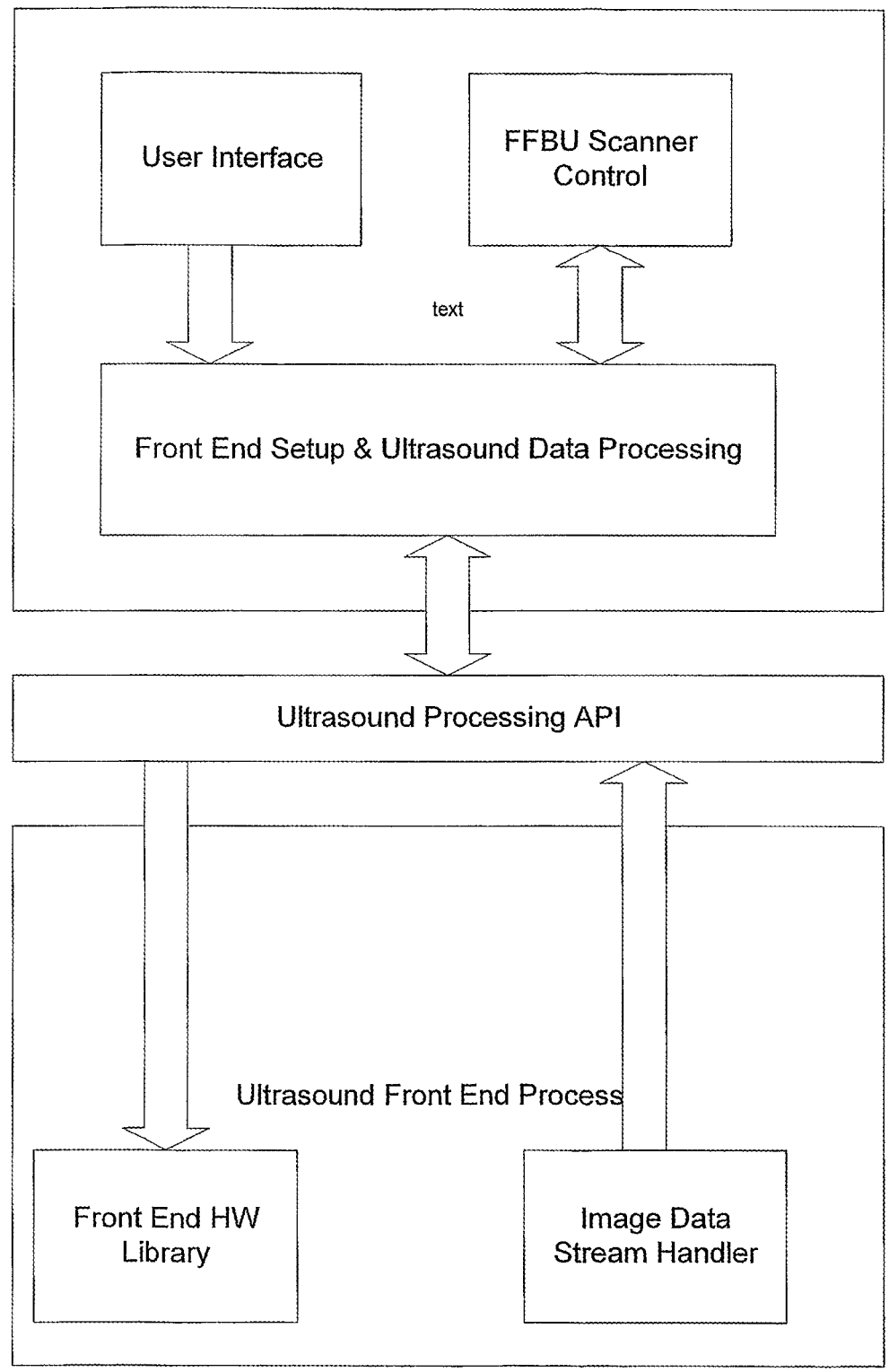
FIG. 6-7 illustrate software interface diagrams according to a preferred embodiment.
Figure 7:
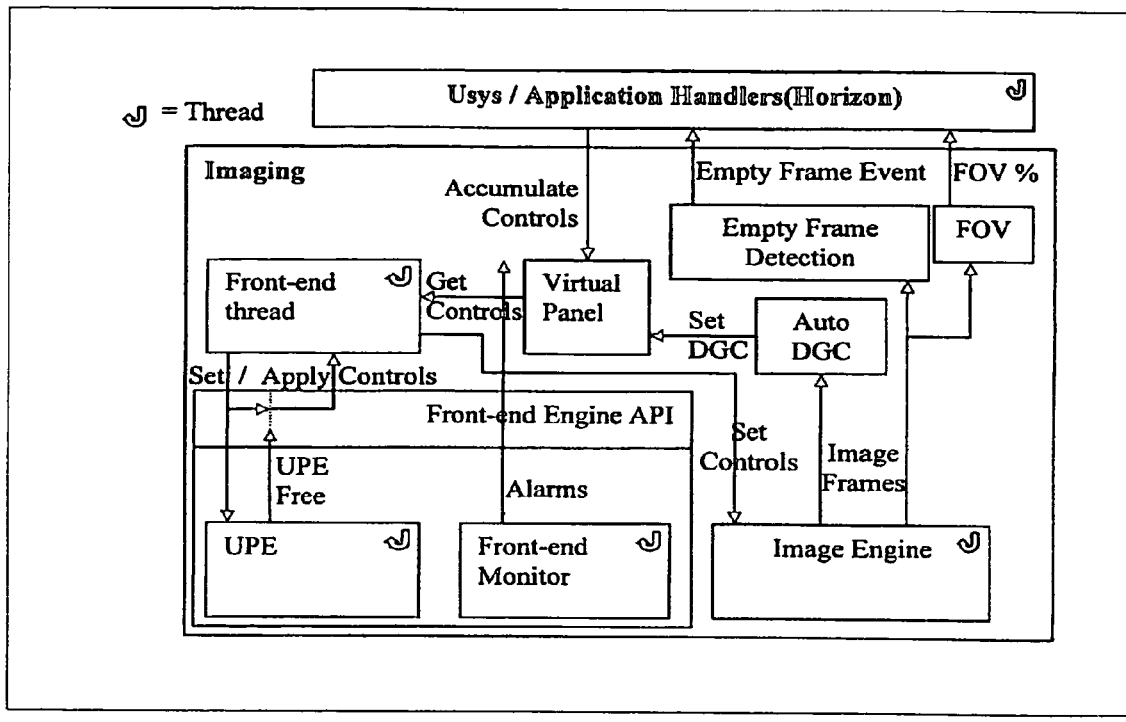

Software interface. See FIG. 6. Ultrasound beamformer independent software generic control interface: Probe insertion/removal detection and notification; Probe and application selection; Scanning modality selection; Ultrasound beam gain/depth calibration; Ultrasound beam lateral field of view control; Ultrasound beam depth control; Ultrasound tissue dependent acquisition parameters; Ultrasound image position tagging; Transducer parameter reprogramming.

Software interface. Mechanical Scanner: Scanner calibration; Scanner reset; Move to X location; Release compression; Turn on pump X; Turn off pump X; Compression pressure reading; Compression separation distance; Compression plate angle; Scanner status. FIG. 8 illustrates components of an imaging system application program interface (API) for an off-the-shelf ultrasound engine according to a preferred embodiment.

Figure 9:
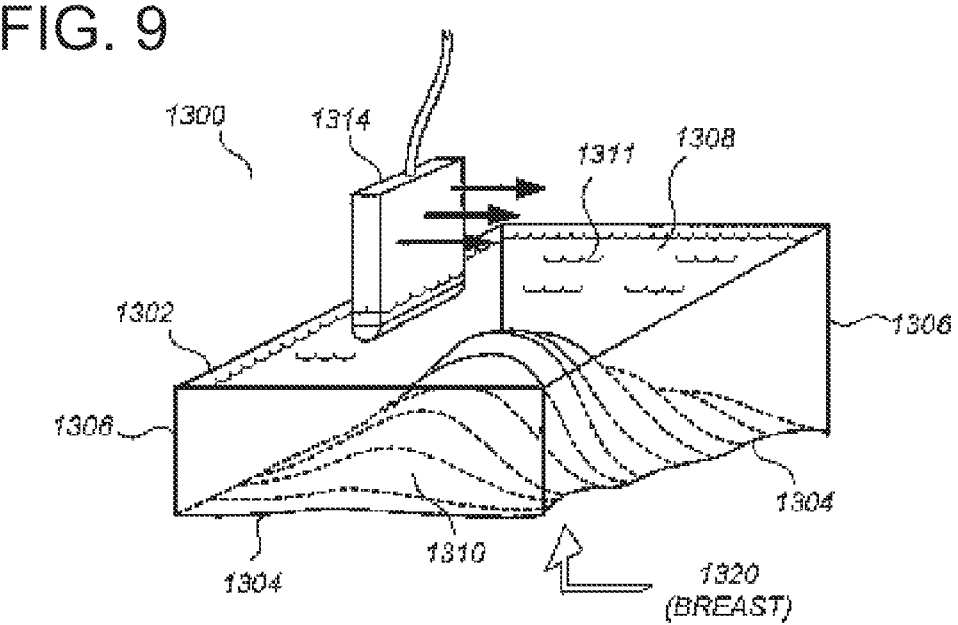
FIG. 9 illustrates a breast ultrasound adapter for facilitating breast ultrasound scans in accordance with a preferred embodiment.

FIG. 9 illustrates a breast ultrasound adapter 1300 for facilitating breast ultrasound scans in accordance with a preferred embodiment. As known in the art, it is required that a close acoustical coupling be maintained between the breast skin surface and the ultrasound probe at all times during the scan. In particular, there should be no vacuum or air pockets anywhere along the path of the interrogating ultrasound pulses. This is usually achieved by keeping the breast surface wet with a water-containing polymeric fluid or gel at all points of contact with the ultrasound probe. Alternatively, gel bags have been placed between the ultrasound probe and skin surface to maintain an acoustic coupling. With both of these methods, however, the breast itself is necessarily shifted around and compressed by differing amounts at differing places as the ultrasound probe is moved.

Breast ultrasound adapter 1300 comprises an upper frame 1302, side walls 1306, and a bottom membrane 1310 forming a fluid reservoir volume 1308 for holding a water-containing polymeric fluid or gel. As shown in FIG. 9, breast ultrasound adapter 1300 has been placed over a breast 1320 and filled with fluid 1311, and the bottom membrane 1310 has conformally adapted to the shape of the breast 1320. The fluid level should rise above the highest point of the breast 1320. The bottom of an ultrasound probe 1314 is submerged in the fluid 1311 and is swept in a lateral direction across the breast as indicated in FIG. 9, the bottom of the ultrasound probe 1314 remaining submerged during the lateral sweep. Preferably, the bottom of ultrasound probe 1314 is maintained in a plane parallel to the fluid surface and does not contact the bottom membrane 1310 during the lateral sweep. Position sensors (not shown) are used to track the position of the ultrasound probe 1314 as it is swept, usually by hand, across the fluid surface. Preferably, water-containing polymeric gel, water, and/or oil are used to improve the contact between the bottom membrane 1310 and the breast 1320. Advantageously, the breast is maintained in a substantially consistent position and in a consistent state of compression during the scanning process, thereby facilitating consistency among the ultrasound slices forming the three-dimensional image volume.

The breast ultrasound adapter 1300 may comprise any of a variety of material configurations that facilitate the presence of an open fluid reservoir above the breast of a supine patient, the fluid reservoir having a lower surface that conforms to the breast shape such that an ultrasound probe is acoustically coupled to the breast skin surface when immersed in the fluid. By way of example, upper frame 1302 is preferably a rigid or semi-rigid compression-molded silicone rubber material, or an equivalent material, such that the breast ultrasound adapter 1300 can be supported and moved by manipulating the upper frame 1302 even when full of fluid. Side walls 1306 may also be rigid or semi-rigid. In the embodiment of FIG. 9, side walls 1306 are semi-rigid and sufficiently flexible such that they are conformal with the patient's skin surface along points of intersection 1304 therewith. However, in alternative preferred embodiments, the side walls 1306 do not contact the skin surface directly and therefore may be rigid. In this case, the bottom membrane protrudes downward from the side walls and hangs down like a plastic bag over the breast when filled with fluid. In still other preferred embodiments, the side walls 1306 are not present at all, and the bottom membrane hangs down directly from the upper frame 1302 over the breast when filled with fluid. In preferred embodiments in which the side walls 1306 do not contact the skin surface directly or are not present, the breast ultrasound adapter 1300 is supported by the upper frame 1302 and laid gently over the breast, which does not support its entire weight. The bottom membrane 1310 preferably comprises a flexible, watertight, conforming material. An at least partially distensible characteristic assists in ensuring bubble-free contact with the breast skin. Suitable materials include protective latex, synthetic elastomers, cellophane, or other protective sheath-type materials described in U.S. Pat. 6,039,694, which is incorporated by reference herein. The respective pieces are fastened together by a suitable adhesive such as silicone RTV.

Figure 10:
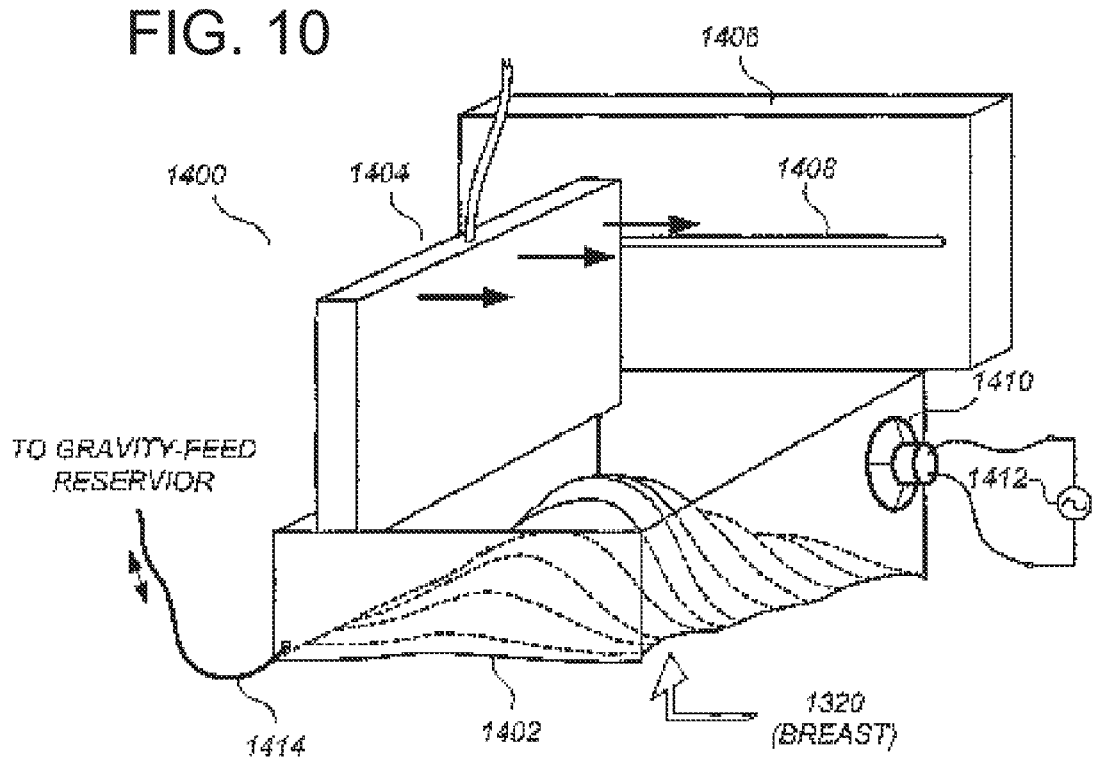
FIG. 10 illustrates a partially automated apparatus for performing breast ultrasound scans in accordance with a preferred embodiment.

FIG. 10 illustrates a breast ultrasound adapter 1402 having additional features in accordance with a preferred embodiment that, in conjunction with a mechanical probe translation assembly, forms a semi-automatic breast ultrasound scanning device 1400. Breast ultrasound adapter 1402 comprises an integrated audio speaker 1410 coupled to an electrical source 1412 for use in vibrational resonance applications. The apparatus of FIG. 10 also comprises a conceptual diagram of an ultrasound probe 1404 as it is guided by a mechanical translator 1406, for example by means of a slot 1408. Advantageously, the probe position may be sensed by mechanical transducers instead of position sensors as required in the embodiment of FIG. 9, supra. The mechanical translator may be affixed to the frame of the breast ultrasound adapter 1402, or may alternatively be externally supported.

Finally, breast ultrasound adapter 1402 further comprises a fluid transport opening and fluid conduit 1414 for coupling to a gravity-feed reservoir (not shown) that is functionally similar to an intravenous (IV) fluid container. In accordance with a preferred embodiment, the gravity-feed reservoir is raised, either by hand or by an automated mechanical assembly, to introduce fluid into the breast ultrasound adapter 1402 after it has been placed on a patient's breast. Following the scan procedure, the gravity-feed reservoir is lowered to cause fluid to drain out, thereby emptying the breast ultrasound adapter 1402. The vertical position of the gravity-feed reservoir may also be adjusted used to regulate the level of the fluid during the scan.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that several ultrasound system ports can be dedicated to FFBU operation to connect more than one FFBU transducer. For example, a first FFBU transducer on the first port can be for a top side scan, while the second FFBU transducer on the second port can be used for the bottom side scan, with images from both being sent to the viewing station. Therefore, reference to the details of the preferred embodiments are not intended to limit their scope, which is limited only by the scope of the claims set forth below.

What is claimed is:

1. A method for modifying a general purpose ultrasound system, the general purpose ultrasound system being conventionally equipped with first and second ports each configured to couple to a hand-held probe, the method comprising:
coupling a hand-held probe to said first port;
coupling a mechanically-driven breast scanning probe to said second port, said mechanically-driven breast scanning probe being a component of a full-field breast ultrasound (FFBU) scanning apparatus including probe driving hardware and associated probe driving circuitry;
compressing a patient's breast with a flexible material sheet configured to contact and chestwardly compress the patient's breast, and scanning the patient's breast with an elongated ultrasonic transducer driven mechanically to scan across the breast while moving in a direction along a chest wall of the patient while sending into the breast and receiving from the breast ultrasound energy passing through said flexible material sheet;
establishing a data communication path between said probe driving circuitry and said general purpose ultrasound system; and
programming said general purpose ultrasound system to accommodate both (i) a first operating mode in which said hand-held probe is operated in a conventional manner and signals therefrom are processed according to a conventional hand-held operation of the general purpose ultrasound system, and (ii) a second operating mode in which said breast scanning probe is mechanically driven under control of the general purpose ultrasound system while signals therefrom are processed by the general purpose ultrasound system to generate FFBU breast image data.

2. The method of claim 1 in which said compressing comprises compressing a supine patient's breast.

3. The method of claim 1 in which said compressing comprises compressing the patient's breast with a flexible material sheet that is not porous to an ultrasound couplant.

4. The method of claim 1 in which said scanning comprises scanning while the ultrasonic transducer is out of physical contact with said flexible material sheet.

5. The method of claim 1, said general purpose ultrasound system having a single ultrasound engine configured to accommodate hand-held ultrasound probes having a predetermined number of transducer elements, said mechanically-driven breast scanning probe being equipped with more transducer elements than said predetermined number, said method further comprising providing sliding-window logic between said mechanically-driven breast scanning probe and said ultrasound engine such that the presence of additional transducer elements is substantially transparent to the operation of said ultrasound engine.

6. The method of claim 5, said general purpose ultrasound system being conventionally equipped with conventional user interface driving software in communication with a user interface, the method further comprising installing a first software switch between said conventional user interface driving software and said user interface, said first software switch maintaining said communication in said first operating mode, said first software switch terminating said communication in said second operating mode and instead maintaining communication between said user interface and an FFBU user interface driving module in said second operating mode, such that said user interface operates according to an FFBU display mode when said general purpose ultrasound system is in said second operating mode.

7. The method of claim 6, said general purpose ultrasound system being conventionally equipped with conventional system/data control software in communication with said ultrasound engine, the method further comprising installing a second software switch between said conventional system/data control software and said ultrasound engine, said second software switch maintaining said communication in said first operating mode, said second software switch terminating said communication in said second operating mode and instead maintaining communication between said ultrasound engine and, an FFBU system/data control module when said general purpose ultrasound system is in said second operating mode.

8. A dual-purpose ultrasound system, comprising:
a general purpose ultrasound system, the general purpose ultrasound system being conventionally equipped with first and second ports each configured to couple to a hand-held probe;
a hand-held probe coupled to said first port;
a full-field breast ultrasound (FFBU) scanning apparatus comprising a mechanically-driven breast scanning probe, probe driving hardware for driving said breast scanning probe, and probe driving circuitry associated with said probe driving hardware, wherein said breast scanning probe is coupled to said second port of said general purpose ultrasound system;
said mechanically driven breast scanning probe comprising a flexible material configured to contact and exert chestward pressure on a patient's breast, and an elongated ultrasonic transducer driven mechanically to scan across the breast while moving in a direction along a chest wall of the patient and to send into the breast and receive from the breast ultrasound energy passing through said flexible material; and
a data communication path between said probe driving circuitry and said general purpose ultrasound system, wherein said general purpose ultrasound system is configured to accommodate both (i) a first operating mode in which said hand-held probe is operated in a conventional manner and signals therefrom are processed according to a conventional hand-held operation of the general purpose ultrasound system, and (ii) a second operating mode in which said breast scanning probe is mechanically driven under control of the general purpose ultrasound system while signals therefrom are processed by the general purpose ultrasound system to generate FFBU breast image data.

9. The dual-purpose ultrasound system of claim 8 in which said mechanically driven breast scanning probe is configured to compress the breast of a supine patient.

10. The dual-purpose ultrasound system of claim 8 in which said mechanically driven breast scanning probe is configured to compress the patient's breast with a flexible material sheet that is not porous to an ultrasound couplant.

11. The dual-purpose ultrasound system of claim 8 in which said ultrasonic transducer is configured to be out of physical contact with said flexible material sheet while scanning the patient's breast.

12. The dual-purpose ultrasound system of claim 8, further comprising a user-controllable switch for causing said system to switch between said first and second operating modes.

13. The dual-purpose ultrasound system of claim 8, said general purpose ultrasound system having a single ultrasound engine configured to accommodate hand-held ultrasound probes having a predetermined number of transducer elements, said mechanically-driven breast scanning probe being equipped with more transducer elements than said predetermined number, said dual-purpose ultrasound system further comprising sliding-window logic along a path between said mechanically-driven breast scanning probe and said ultrasound engine such that the presence of additional transducer elements is substantially transparent to the operation of said ultrasound engine.

14. The dual-purpose ultrasound system of claim 13, said general purpose ultrasound system being conventionally equipped with conventional user interface driving software in communication with a user interface, further comprising a first software switch between said conventional user interface driving software and said user interface, said first software switch maintaining said communication in said first operating mode, said first software switch terminating said communication in said second operating mode and instead maintaining communication between said user interface and an FFBU user interface driving module in said second operating mode, such that said user interface operates according to an FFBU display mode when said general purpose ultrasound system is in said second operating mode.

15. The dual-purpose ultrasound system of claim 14, said general purpose ultrasound system being conventionally equipped with conventional system/data control software in communication with said ultrasound engine, further comprising a second software switch between said conventional system/data control software and said ultrasound engine, said second software switch maintaining said communication in said first operating mode, said second software switch terminating said communication in said second operating mode and instead maintaining communication between said ultrasound engine and an FFBU system/data control module when said general purpose ultrasound system is in said second operating mode.

16. A full-field breast ultrasound (FFBU) toolkit for adapting and integrating a general purpose ultrasound system into a dual-purpose ultrasound system, the general purpose ultrasound system being conventionally equipped with first and second ports each configured to couple to a hand-held probe, the FFBU toolkit comprising:
a full-field breast ultrasound (FFBU) scanning apparatus comprising a mechanically-driven breast scanning probe, probe driving hardware for driving said breast scanning probe, and probe driving circuitry associated with said probe driving hardware, wherein said breast scanning probe is configured to couple to the second port of the general purpose ultrasound system;
said mechanically driven breast scanning probe comprising a flexible material configured to contact and exert chestward pressure on a patient's breast, and an elongated ultrasonic transducer driven mechanically to scan across the breast while moving in a direction along a chest wall of the patient and to send into the breast and receive from the breast ultrasound energy passing through said flexible material;
a facility configured for establishing a data communication path between said probe driving circuitry and the general purpose ultrasound system; and
a facility configured for programming said general purpose ultrasound system to accommodate both (i) a first operating mode in which a hand-held probe coupled to the first port is operated in a conventional manner and signals therefrom are processed according to a conventional hand-held operation of the general purpose ultrasound system, and (ii) a second operating mode in which said breast scanning probe is coupled to said second port and is mechanically driven under control of the general purpose ultrasound system while signals therefrom are processed by the general purpose ultrasound system to generate FFBU breast image data.

17. The FFBU toolkit of claim 16 in which said mechanically driven breast scanning probe is configured to compress the breast of a supine patient.

18. The FFBU toolkit of claim 17 in which said ultrasonic transducer is out of physical contact with said flexible material sheet while scanning the patient's breast.

19. The FFBU toolkit of claim 16, further comprising a facility configured for equipping said dual-purpose ultrasound system with a user-controllable switch for causing said dual-purpose ultrasound system to switch between said first and second operating modes.

20. The FFBU toolkit of claim 16, said general purpose ultrasound system being conventionally equipped with conventional user interface driving software in communication with a user interface, said FFBU toolkit further comprising a facility configured for equipping said dual-purpose ultrasound system with a first software switch between said conventional user interface driving software and said user interface, said first software switch maintaining said communication in said first operating mode, said first software switch terminating said communication in said second operating mode and instead maintaining communication between said user interface and an FFBU user interface driving module in said second operating mode, such that said user interface operates according to an FFBU display mode when said general purpose ultrasound system is in said second operating mode.

* * * * *

UNITED STATES PATENT AND TRADEMARK OFFICE
CERTIFICATE OF CORRECTION

| | | |
|---|---|---|
| PATENT NO. | : 8,747,317 B2 | Page 1 of 1 |
| APPLICATION NO. | : 13/685064 | |
| DATED | : June 10, 2014 | |
| INVENTOR(S) | : Zengpin Yu et al. | |

It is certified that error appears in the above-identified patent and that said Letters Patent is hereby corrected as shown below:

On the Title Page, Item (54) and in the Specification, Column 1, Line 2, the title, delete "Architechture" and insert --Architecture--.

Signed and Sealed this
Sixteenth Day of September, 2014

Michelle K. Lee
*Deputy Director of the United States Patent and Trademark Office*